United States Patent [19]

Grigorov et al.

[11] 4,287,896
[45] Sep. 8, 1981

[54] ELECTRODE FOR CONNECTING TO AN INTERNAL ORGAN OF HUMAN BODY

[76] Inventors: Sergei S. Grigorov, prospekt Vernadskogo, 105, korpus 2, kv. 81, Moscow; Ravil N. Nazyrov, MIZ, 31, kv. 1, Mozhaisk, both of U.S.S.R.

[21] Appl. No.: 68,524

[22] Filed: Aug. 22, 1979

[51] Int. Cl.³ ............................................. A61N 1/04
[52] U.S. Cl. ................................ 128/786; 128/419 P
[58] Field of Search .................... 128/419 P, 784–786, 128/642

[56] References Cited

U.S. PATENT DOCUMENTS

| | | | |
|---|---|---|---|
| 3,568,660 | 3/1971 | Crites et al. | 128/786 |
| 4,030,508 | 6/1977 | Thalen | 128/786 |
| 4,106,512 | 8/1978 | Bisping | 128/785 |
| 4,156,429 | 5/1979 | Amundson | 128/419 P |

Primary Examiner—Lee S. Cohen
Attorney, Agent, or Firm—Robert E. Burns; Emmanuel J. Lobato; Bruce L. Adams

[57] ABSTRACT

The electrode having a tubular indulative body accomodating an electrical supply lead made as a coil spring rigidly coupled to distal and contact heads, both accomodated in the body at opposite ends thereof. The opposite end portions of the coil spring have a length not exceeding twice the distance from the place of contact of the contact head with the interior portion of the organ, to the place where the electrode emerges from said organ, the coils of the coil spring are spaced in a close proximity to one another. On a middle portion of the coil spring the coils are spaced with a pitch that provides for a longitudinal stability of the electrode while being passed via a transvenous route to be implanted in an organ involved.

3 Claims, 4 Drawing Figures

ELECTRODE FOR CONNECTING TO AN INTERNAL ORGAN OF HUMAN BODY

FIELD OF THE INVENTION

This invention relates generally to medical apparatus and instruments and more specifically to an electrode for connecting to an internal organ of a body.

The electrode proposed herein is adapted for conducting electric pulses from a source of power to the organ of a body, and can find application for stimulating both cardiac action and the action of some other internal organs of humans.

BACKGROUND OF THE INVENTION

Inasmuch as the storage capacity of sources of electric power is not large at best electrodes for the purpose of devices such as those of the invention are such as to be economical as to the current drained. One of the possible ways of developing such electrodes is to reduce the ohmic resistance thereof. This can be attained first by selecting a material having low ohmic resistance and secondly due to an appropriately provided electrode construction.

Known in the present state of the art are electrodes whose current supplying lead is made of materials having low ohmic resistance (cf., e.g., "Engineering Analysis of Pacemaker Electrodes" by Daniel W. van Heeckeren and James F. Hogan, Annals of New York Academy of Sciences, 1969, v. 167, p.p. 774–784). Pertaining to such materials are, for example, the alloys of the following weight percent composition:

|            |           |      |       |
|------------|-----------|------|-------|
|            | platinum  | 90.0 |       |
|            | iridium   | 10.0 | (I)   |
| as well as | palladium | 35.0 |       |
|            | silver    | 30.0 |       |
|            | copper    | 14.0 | (II)  |
|            | platinum  | 10.0 |       |
|            | gold      | 10.0 |       |
|            | zinc      | 1.0  |       |

In addition, used as such a material is stainless steel clad with gold and platinum.

However, all these materials incorporate highly expensive rare metals and feature low mechanical fatigue as compared to an alloy extensively applied for the purpose currently; said alloy is based on cobalt and has the following weight percent composition:

|            |       |       |
|------------|-------|-------|
| cobalt     | 40.0  |       |
| chromium   | 20.0  |       |
| nickel     | 15.0  |       |
| molybdenum | 7.0   |       |
| manganese  | 2.0   | (III) |
| carbon     | 0.15  |       |
| beryllium  | 0.04  |       |
| iron       | 15.81.|       | the above alloy though being inferior to the afore-mentioned ones as to ohmic resistance has much higher endurance. Thus, electrodes made of the alloy (III), under otherwise equal operating conditions, prove to be 330 times more durable than electrodes made of the alloy (I).

Some electrodes are known to be in current use, wherein a reduced ohmic resistance is achieved due to appropriately selected construction of the electrode.

Thus, e.g., 49-conductor braided stainless electrodes are available from "General Electric Co.", while the firm "Electric" produces 49-conductor braided electrodes made of gold- and platinum-clad stainless steel. However, the former electrodes are 25 times and the latter, 5 times less durable than the electrodes whose current-supply lead is a coil winding featuring its coils wound closely to one another (cf., e.g., the afore-mentioned article "Engineering Analysis of Pacemaker Electrodes").

Some attempts are known to have been made to provide a current-supply electrode lead as a few (e.g., four) parallel wound coil springs (multiple-coil winding) as this substantially reduces the ohmic resistance of a current conductor (cf., e.g., W. Irnich "Engineering concepts of pacemaker electrodes", "Engineering in Medicine", 1, "Pacemaker Technology", Berlin-Heidelberg-New York, 1975).

The author claims that such a construction is not only instrumental in reducing the ohmic resistance of the supply lead (which proves to be an indisputable fact) but also provides for an adequate flexibility and an increased endurance of the electrode. The author explains the fact by that all the four coil springs would have to break before the electrode fails. It is quite evident, however, that a maximum flexibility is attained (with other things being equal) when the coils are wound as closely as possible to one another, i.e., when the winding pitch equals the diameter of the wire conductor being wound (i.e., $t \approx d$), which is attainable in the case of a single-layer winding. A two- or multi-layer winding will affect adversely the flexibility of the electrode. A multi-layer winding augments the coil-to-coil spacing (or winding pitch) multiply, thus approximating the coil rod to the straight elastic bar and thereby adding very much to the flexural rigidity of the conductor, which reduces considerably the endurance fatigue of the coils of any of several windings. It ensues from all the discussed above that failure of any separate coil occurs much earlier than in the case of a single-layer winding having the coils spaced as close as possible to one another. If only a single coil fails its sharp and rough edges will rub against the other coils, thus causing an intense fatigue wear and breakdown of the latter.

The problem of devising extensible electrodes is far from being solved at present altogether. Practically the problem is being solved due to diverse surgical techniques and approaches, such as the provision of semiloop-like (loosely hanging) excess conductor lengths inside and close to the organ, as well as along the transvenous route and at the place of connection of the distal electrode head to the source of power supply, or by replacing the electrode after a definite lapse of time (in cases where the electrode has been implanted in a growing organism).

However, such approaches can solve the problem but incompletely as the provision of semiloop-like excess conductor lengths is not feasible in all cases (e.g., in the case of small-diameter veins) and is of low efficacy as the electrode body is liable to get enveloped in fat and other cells and becomes of low mobility as to length direction. On the other hand periodic replacement of the electrodes requires further expenses for a corresponding operation and fresh electrodes.

Another electrode for connecting to an internal organ of human body is known to comprise a body accomodating a supply lead shaped as a coil spring rigidly coupled to the distal and contact heads thereof which are located at the ends of said body, the coils of the spring on the faces thereof are spaced as close as possible to one another (cf., e.g., model 6905, 6907 endocardial monopolar electrodes available from "Medtronic Co.", USA).

In the latter electrode the coils of a coil spring are arranged in a nearest proximity to one another throughout the spring length, i.e., with the same pitch along the entire length thereof. The electrode body is made as a plain-walled tube from a dielectric material.

Such an electrode features high ohmic resistance of the wire lead thereof which results in a high-rate exhaustion of the source of electric power (such as the battery of a pulse generator) and results in a higher threshold of electric stimulation of the organ involved. The electrode requires extensive consumption of precious metals (platinum, silver) from which the supply lead of a majority of electrode modifications is made. In addition, the electrode is inadequately extensible lengthwise in the course of operation which might result later in its lengthwise displacement and separation of the electrode contact head from the place of contact with the organ involved (e.g., several years after the implanting), which is likely to occur most commonly with the implanting is in a growing organism, or as a result of apparent changes in the patient's stature or of abrupt motions of the patient e.g., during sports games, while dancing or as a result of falls. In all these cases the contact head of the electrode is liable to displace, whereby an ineffective stimulation occurs in some attitudes of the patient's body.

SUMMARY OF THE INVENTION

It is an object of the present invention to provide an electrode for connecting to an internal organ of a body, which features a low ohmic resistance of the supply lead thereof.

It is another object of the present invention to reduce the consumption of a precious metal for making the electrode supply lead.

It is another object of the present invention to provide an electrode featuring more extensibility as for length.

The objects are accomplished due to the fact that in an electrode for connecting to an internal organ of the body, according to the invention comprises a body accomodating a supply lead shaped as a coil spring rigidly coupled to the distal and contact heads of the electrode, which are located in said body at the ends thereof. The coils or convolutions of the spring on the face portions thereof are spaced as close as possible to one another, according to the invention the coils of the coil spring on its middle portion confined within the end faces thereof are spaced with a pitch that provides for a longitudinal stability of the electrode while it is being passed along the transvenous route for placing inside the organ involved. The length of the face portions of the spring do not exceed double the distance from the place of contact of the electrode contact head with the interior of the organ involved, to the place where the electrode emerges from the organ.

It is expedient that the coil spring should comprise two transient portions located between a respective face portion and the middle portion thereof and that the coils on the transient portions be spaced with a pitch regularly increasing over the amount of spacing of the coils on the face portions to that of the coils of the middle portion of the spring.

It is also expedient that the electrode body be made corrugated on its portion corresponding to that of the coil spring located between its face portions.

A key parameter of electric stimulation is current density, i.e., the higher the current density the more effective the stimulation; one of the possible ways to attain this effect is a reduced ohmic resistance of the supply lead which is the case with the herein-proposed electrode due to a different winding pitch of the coil spring on various portions thereof. The proposed electrode enables one to make use of electric power sources featuring low power output and hence having longer service life which is essential as the now-existing pulse generators are restricted as to power they provide. The supply lead of the proposed electrode requires less precious metal for the manufacture thereof which is likewise due to the provision of a middle and transient portions of the coil spring. Even when alloys incorporating precious metals are applied their consumption is half as much under otherwise equal operating conditions. A possibility arises to apply on a larger scale non-critical alloys instead of precious metals, such as cobalt-based alloys, without affecting the endurance and functional feature of the electrode, viz., its flexibility. The electrode is characterized by an adequate longitudinal extensibility while in operation, this is due to a corrugated portion of the electrode body. A sufficient extensibility of the proposed electrode renders less possible its later longitudinal displacement and enables a higher stimulating effect to be obtained in time when implanting the electrode in a growing organism and/or in the case of abrupt motions of the patient.

BRIEF DESCRIPTION OF THE DRAWINGS

In what follows the invention will be explained in a disclosure of some specific exemplary embodiments thereof with reference to the accompanying drawings, wherein.

DESCRIPTION OF THE PREFERRED EMBODIMENTS

Figure 1:
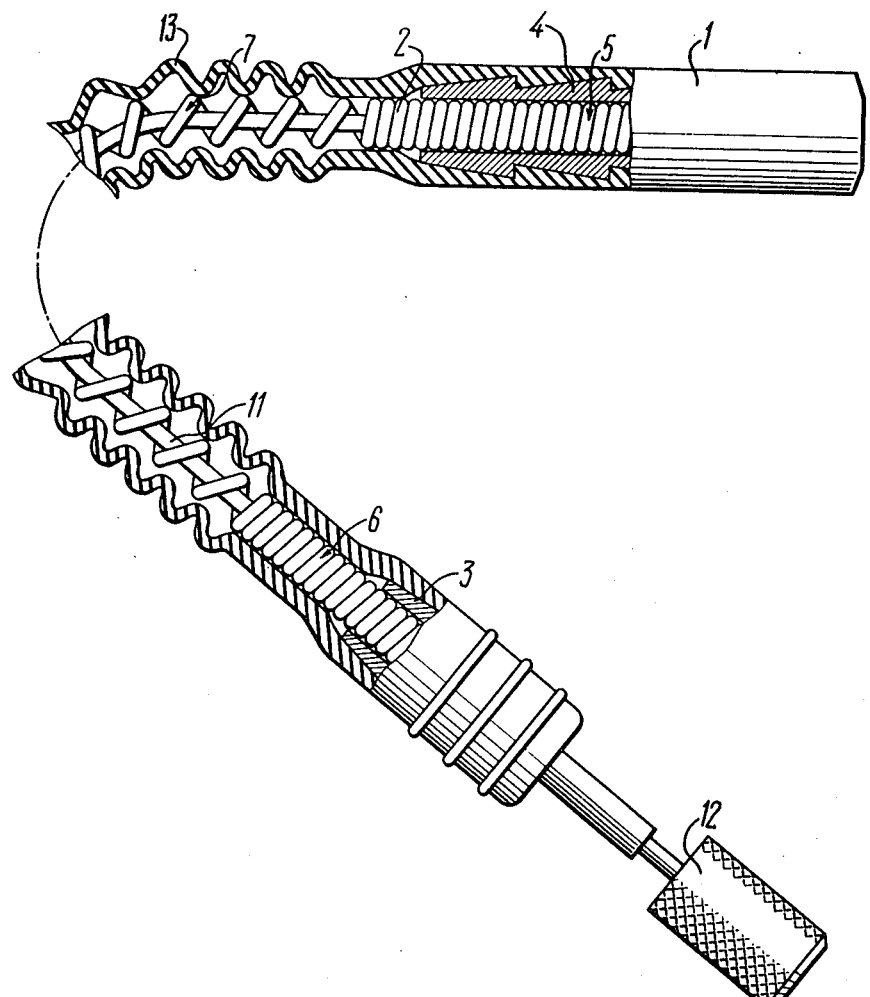
FIG. 1 is a fragmentary longitudinal view partly in section of an electrode body and the distal and contact heads thereof, according to the invention.

The electrode for connecting to an internal organ of a body comprises a body 1 (FIG. 1) accomodating a supply lead shaped as a coil spring 2 rigidly coupled to a distal head 3 and a contact head 4, both of them being located in the body 1 at the ends thereof. The coils of the coil spring 2 on end portions 5, 6 are in a close proximity to one another, the winding pitch t being equal to the wire diameter d in this particular case. The coils of the coil spring 2 located on a middle portion 7 between the end portions 5, 6 are spaced apart with a pitch that provides for the longitudinal stability of the electrode when conducted along a transvenous route 8

Figure 2:
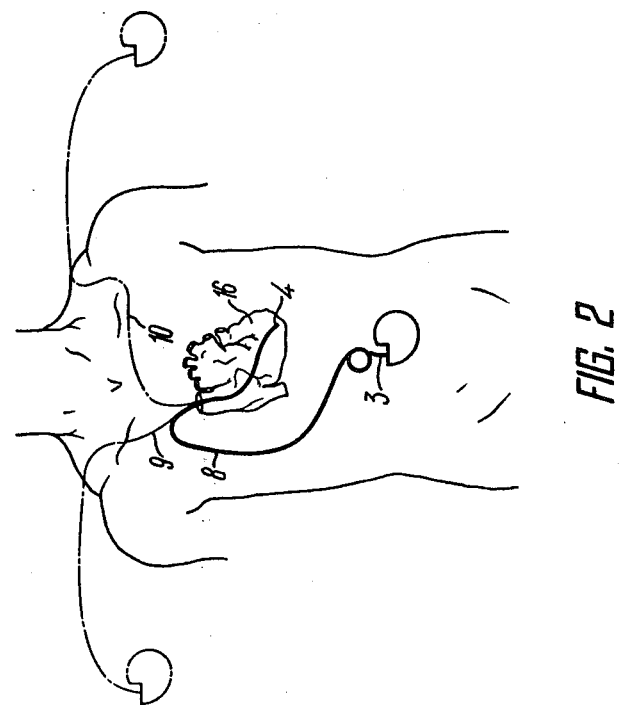
FIG. 2 is a diagram illustrating the arrangement of the electrode in a human body for electrocardiostimulation, according to the invention.

(FIG. 2), 9, 10. The pitch t on the portion 7 (FIG. 1) can be selected to be, say, within 4 to 6 mm.

Positioning of the electrode in the organ to be stimulated is carried out by a stylet 11 having a knob 12.

Figure 3:
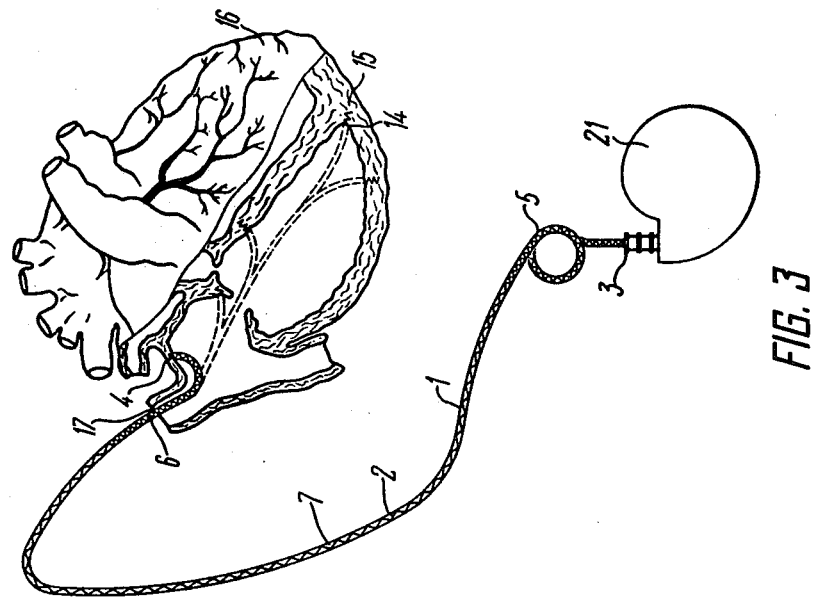
FIG. 3 is a schematic view of the electrode, according to the invention, while made fast with its contact head on the apex of the right cardiac ventricle, variants of fastening the electroe to the other cardiac portions.

As can be seen from FIG. 3 the electrode body 1 is plain-walled along the entire length thereof. However, in order to attain an adquate longitudinal extensibility of the electrode while in operation, which is especially the case with a growing organism, the body 1 is expedient to have a portion 13 (FIG. 1) corresponding to the portion 7 of the coil spring 2, corrugated, whereas its end portions are plain-walled.

The length of the end portions 5, 6 of the coil spring 2 is selected so as to suit individual anatomical features of the organism, such as its dimensions, and structure, and is not in excess of a doubled distance from a place 14 (FIG. 3) of contact of the contact head 4 with the interior of the organ involved (in the present particular case, the apex of the righ ventricle 15 of a heart 16), to a place 17 where the electrode emerges from the organ involved, i.e., the heart 16. The distance as a rule does not exceed 100 to 150 mm.

Figure 4:
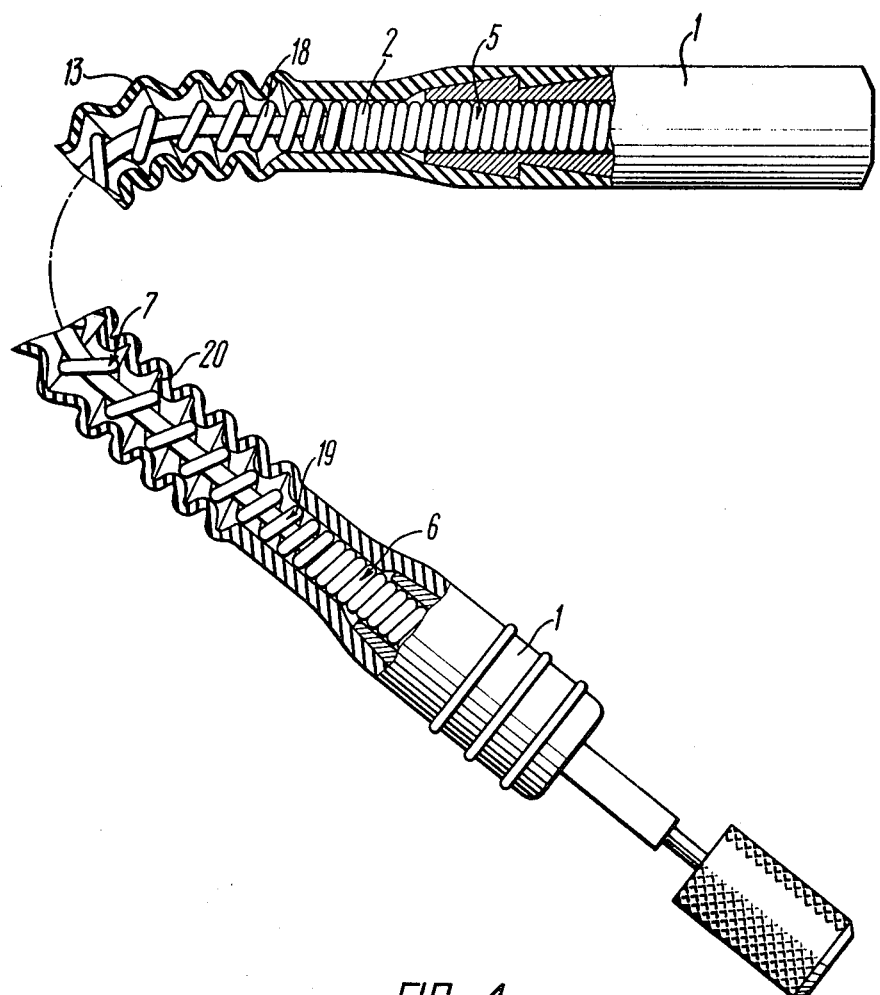
FIG. 4 is a fragmentary view of FIG. 1 showing the transient portions of the coil spring and the corrugated portion of the electrode body arranged along a helical line, according to the invention.

To enhance the strength of the coil spring 2 (FIG. 4) at the place where the portions 5, 6 pass into the portion 7, it is expedient that two transient portions 18, 19 be provided, located between the corresponding end portions 5, 6 and the middle portion 7. The coils of the coil spring 2 on said transient portions 18, 19 are spaced with a pitch regularly increasing from the amount of spacing of the coils on the end portions 5, 6 to that of the coils of the middle portion 7.

The corrugations on the portion 13 of the body 1 may be arranged along a helical line 20.

To effect stimulation of the organ the distal head 3 (FIG. 3) is connected to a source of electric power, viz., an electrocardiostimulator 21 in this particular case.

The electrode for connecting to an internal organ of a body operates as follows.

The electrode is conducted along the transvenous route 8 (FIG. 2) 9 or 10 into the interior of the organ involved, viz., the heart 16, with the aid of the stylet 11 (FIG. 1), and its contact head 4 is fastened to the tissue of the heart 16 at the places shown in FIG. 3. Once the head 4 has been made fast the stylet 11 (FIG. 1) is removed. Then the distal head 3 is connected to a power source, viz. the electrocardiostimulator 21 (FIG. 3). In this position an electrostimulation system "power source-wire conductor—organ" is considered to have been implanted. The body 1 made of a dielectric material protects the coil spring 2, the contact head 4 and the distal head 3 against the effect of the surrounding medium.

The corrugated portion 13 (FIGS. 1, 4) of the body 1 is located between the contact head 4 and the distal head 3 approximately 150 mm away from the faces. The coil spring 2 is wound with a pitch from 4 to 6 mm on the respective portion 7.

On the portions 5, 6 of the coil spring 2 the coils are spaced most proximal to one another as high mechanical stresses are liable to arise at that place and to break the supply lead. The closely wound coils on the portions 5, 6 pass into the coils on the portion 7 of the coil spring in a smooth regular way to obey, say, the linear law.

Provision of the coil spring with different pitch as for its length results in a changed ohmic resistance of the electrode, as well as in saving of the material the electrode is made from, which is frequently made of precious metals (gold, platinum, silver).

A principal advantage of the proposed electrode is a reduced stimulation threshold and an increased stimulating effect due to a reduced ohmic resistance of the supply lead. In addition, this enables the service life of the power source and of the electrode intself to be substantially increased.

Provision of the dielectric covering of the electrode body shaped as corrugations adds much to the elasticity and reliability of implanting the electrode in the tissue of the organ involved, as well as improves its performance characteristics, especially in patients who lead an active mode of life or in those who undergo age-dependent changes.

What is claimed is:

1. An electrode for connecting to an internal organ of a human comprising, an insulative tubular body, an electrically conductive coil spring lead extending axially in said body, an electrically conductive distal head in said body at one end and electrically coupled to said coil spring lead, an electrically conductive contact head at an opposite end of said body electrically coupled to said coil spring lead, opposite end portions of said coil spring lead having the coils thereof closely adjacent one another, said end portions not exceeding a length twice the distance from a point of contact of said head with the internal organ to a point where the electrode emerges from said internal organ, a middle portion of said coil spring lead between said end portions, the coils of said middle portion having a pitch greater than the pitch of the coils of said end portions and effective to provide a longitudinal stability of the electrode while being implanted in said human along an intravenous route, and said tubular body comprising a corrugated portion in correspondence with said middle portion of said coil spring lead.

2. An electrode for connecting to an internal organ of a human according to claim 1, in which said coil spring lead comprises two transient portions each disposed between said middle portion and a corresponding end portion of said coil spring lead, each transient portion having coils the pitch of which progressively increases away from the end portions and toward the coils of said middle portion.

3. An electrode for connecting to an internal organ of a human according to claim 2, in which said tubular body comprises said corrugated portion in correspondence with said middle portion and both transient portions of said coil spring lead.

* * * * *